US00PP26740P3

(12) United States Plant Patent
Klemm et al.

(10) Patent No.: US PP26,740 P3
(45) Date of Patent: May 17, 2016

(54) ***DIANTHUS* PLANT NAMED 'KLEDG13158'**

(50) Latin Name: ***Dianthus* sp.**
Varietal Denomination: KLEDG13158

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 105 days.

(21) Appl. No.: 14/120,505

(22) Filed: May 27, 2014

(65) Prior Publication Data
US 2015/0351300 P1 Dec. 3, 2015

(51) Int. Cl.
*A01H 5/02* (2006.01)

(52) U.S. Cl.
USPC ..... Plt./282

(58) Field of Classification Search
USPC ..... Plt./272, 282
See application file for complete search history.

*Primary Examiner* — Susan McCormick Ewoldt
(74) *Attorney, Agent, or Firm* — Barbara Campbell; Bethany R. Roahrig; Cochran Freund & Young, LLC

(57) ABSTRACT

A new *Dianthus* plant particularly distinguished by single-type pink flowers with purple eyes, good branching, and an upright and bushy plant habit, is disclosed.

1 Drawing Sheet

Genus and species: *Dianthus* sp.
Variety denomination: 'KLEDG13158'.

BACKGROUND OF THE NEW PLANT

The present invention comprises a new and distinct variety of *Dianthus*, botanically known as *Dianthus* sp., and hereinafter referred to by the variety name 'KLEDG13158'. 'KLEDG13158' originated from a cross-pollination between the proprietary female *Dianthus* parent 'DSS 2007 0051' (unpatented) and proprietary male *Dianthus* parent 'DSS 2008 0015' (unpatented) in June 2009 in Stuttgart, Germany.

The seeds from the cross were sown and plants were grown in a greenhouse for evaluation, where an individual plant designated 'KLEDG13158' was selected from the group of plants June 2010 in Stuttgart, Germany. In June 2010, 'KLEDG13158' was first vegetatively propagated by vegetative cuttings. 'KLEDG13158' was found to reproduce true to type in successive generations of asexual propagation in Stuttgart, Germany via vegetative cuttings.

SUMMARY

The following are the most outstanding and distinguishing characteristics of this new variety when grown under normal horticultural practices in Stuttgart, Germany.

1. Single-type pink flowers with purple eyes;
2. Good branching; and
3. An upright and bushy plant habit.

CROSS-REFERENCE TO RELATED APPLICATIONS

A Community Plant Variety Rights application was filed with the European Community Plant Variety Rights Office on Jul. 1, 2013, Application No. 2013/1808; and a Plant Breeders Rights application was filed in Switzerland on May 31, 2013.

'KLEDG13158' has not been sold or made publicly available more than one year prior to the filing date of the present application.

DESCRIPTION OF THE PHOTOGRAPH

This new *Dianthus* plant is illustrated by the accompanying photograph of a plant approximately 4 to 5-months old and grown in a glass greenhouse in Stuttgart, Germany. The photograph shows the whole plant, including the flowers and foliage and buds and was taken in April 2011 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDG13158'. The data which define these characteristics were collected from asexual reproductions carried out in Stuttgart, Germany. Data was collected on 4-month old plants grown in a greenhouse in March 2014. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Garden carnation.
- *Designation*.—'KLEDG13158'.

Parentage:
- *Female parent*.—The proprietary *Dianthus* variety 'DSS 2007 0051' (unpatented).
- *Male parent*.—The proprietary *Dianthus* variety 'DSS 2008 0015' (unpatented).

Plant:
- *Propagation type*.—Vegetative cuttings.
- *Time to produce a rooted young plant*.—20 days.
- *Root description*.—White, well-branched, and fine.

*Rooting habit*.—Lanceolate.
*Plant form*.—Potted and garden plant, upright and bushy.
*Plant height*.—15.0 cm.
*Plant diameter or spread*.—16.0 cm.

Lateral branches:
*Length*.—6.0 cm.
*Diameter*.—2.0 cm.
*Internode length*.—1.3 cm.
*Number of internodes per branch*.—3.
*Branch/stem*.—Is solid.
*Node length*.—0.5 cm.
*Node diameter*.—0.4 cm.
*Texture*.—Smooth.
*Color*.—RHS 137D.

Foliage:
*Arrangement*.—Opposite.
*Length*.—5.0 cm.
*Width*.—0.4 cm.
*Shape*.—Lanceolate.
*Apex*.—Acute.
*Base*.—Obtuse.
*Margin*.—Entire.
*Texture* (*both upper and lower surfaces*).—Smooth.
*Immature leaf color*.—Upper surface: RHS 139C. Lower surface: RHS 139D.
*Mature leaf color*.—Upper surface: RHS 139C. Lower surface: RHS 139D.
*Venation pattern*.—Pinnate.
*Venation color* (*both upper and lower surfaces*).—RHS 139C.

Flowers:
*Flower type and habit*.—Single.
*Fragrance*.—Present.
*Natural flowering season*.—Spring to fall.
*Flower longevity*.—6 to 8 days.
*Position of the flowers relative to the foliage*.—Moderately above.
*Buds*.—Length: 1.4 cm. Diameter: 0.5 cm. Shape: Tall cylinder to ovate. Color: RHS 187A. Extrusion of the styles at the bud stage: Styles are included in bud; not visible.
*Corolla*.—Quantity of petals and arrangement: 5 arranged radially. Corolla height: 1.0 cm. Petal length: 3.3 cm. Petal width: 2.0 cm. Petal shape: V-shaped. Petal apex: Obtuse. Petal base: Cuspidate. Petal margin: Serrate. Petal texture (both upper and lower surfaces): Smooth. Petal color: Immature: Upper surface: RHS 60A and RHS 63B. Lower surface: RHS N74C. Mature: Upper surface: RHS 60A and RHS 63C. Lower surface: RHS N74D.
*Calyx*.—Quantity of sepals and arrangement: Composed of 5 sepals. Calyx height: 1.5 cm. Calyx diameter (at the apex): 0.5 cm. Shape: Cylindrical. Sepal texture (both upper and lower surfaces): Smooth. Sepal color: Upper surface: RHS 187B. Lower surface: RHS 177A.

Peduncles:
*Length*.—10.0 cm.
*Diameter*.—0.2 cm.
*Strength*.—Moderate.
*Texture*.—Smooth.
*Color*.—RHS N138D.

Reproductive organs:
*Stamens*.—Quantity per flower: 5. Filament length: 1.0 cm. Filament color: RHS 69D. Anther length: 0.2 cm. Anther diameter: 0.08 cm. Anther color: RHS 84D. Pollen amount: Moderate.
*Pistils*.—Quantity per flower: 2. Pistil length: 2.0 cm. Style length: 0.1 cm. Style color: RHS 73D. Stigma shape: Filamentous. Stigma color: RHS 59C. Ovary size: 0.6 cm. Ovary shape: Ovate. Ovary color: RHS 139D.

Fruit and seed set: Seeds sometimes observed, but no additional information is available.

Disease and pest/insect resistance: No disease and pest/insect resistance observed.

COMPARISON WITH PARENTAL LINES AND KNOWN VARIETY

'KLEDG13158' is a distinct variety of *Dianthus* and is distinguished from its parents as described in Table 1.

TABLE 1

Comparison with Parental Lines

| Characteristic | 'KLEDG13158' | Female Parent 'DSS 2007 0051' | Male Parent 'DSS 2008 0015' |
|---|---|---|---|
| Flower color | Pink with purple eye | Dark pink | Light pink |
| Branching | Very good | Medium | Medium |

'KLEDG13158' is a distinct variety of *Dianthus* and is most similar to the commercial *Dianthus* variety 'KLEDG10117' (U.S. Plant Pat. No. 23,330), also commercially known as Everlast™ 'Lavender+Eye'. Differences between the varieties are described in Table 2.

TABLE 2

Comparison with Similar Variety

| Characteristic | 'KLEDG13158' | 'KLEDG10117' |
|---|---|---|
| Flower color | Pink with purple eye | Lavender with purple eye |
| Plant height | High | Medium |
| Flower type | Single | Double |

We claim:

1. A new and distinct variety of *Dianthus* plant designated 'KLEDG13158' as illustrated and described herein.

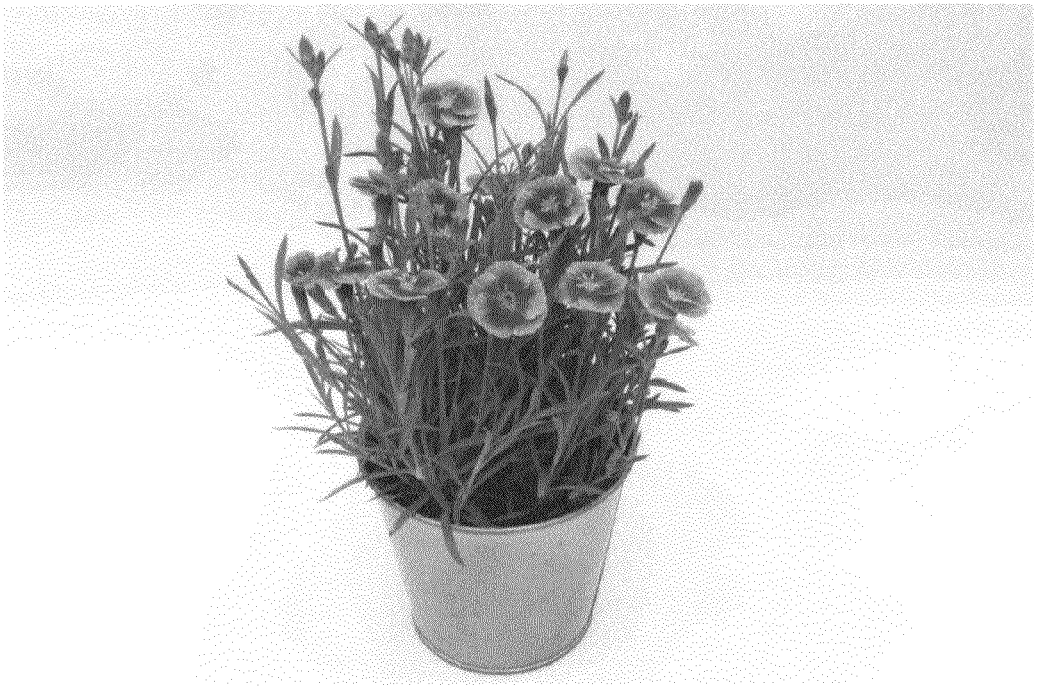

* * * * *